United States Patent [19]

Brown

[11] 4,309,993

[45] Jan. 12, 1982

[54] LIQUID FLOW SENSING APPARATUS

[75] Inventor: Richard I. Brown, Northbrook, Ill.

[73] Assignee: Baxter Travenol Laboratories, Inc., Deerfield, Ill.

[21] Appl. No.: 127,554

[22] Filed: Mar. 6, 1980

[51] Int. Cl.³ .................. A61M 5/00; G01L 9/10; H01H 35/40; F04B 49/06

[52] U.S. Cl. .................. 128/214 E; 73/728; 200/81 R; 200/81.9 R; 417/45; 361/180; 338/32 R

[58] Field of Search .................. 361/180; 335/100; 340/608; 338/32 R; 128/214 E, 1 D; 200/81.9 R, 83 R, 81 R; 417/43, 45; 73/728

[56] References Cited

U.S. PATENT DOCUMENTS

| | | | |
|---|---|---|---|
| 2,847,562 | 8/1958 | Marquardt | 361/180 |
| 2,885,506 | 5/1959 | Anderson . | |
| 3,167,691 | 1/1965 | Halista | 361/180 |
| 3,413,095 | 11/1968 | Bramson . | |
| 3,423,551 | 1/1969 | Starbuck . | |
| 3,424,883 | 1/1969 | Heskett . | |
| 3,827,828 | 8/1974 | Edwards . | |
| 3,833,013 | 9/1974 | Leonard . | |
| 3,841,157 | 10/1974 | Willock | 128/214 E |
| 3,907,504 | 9/1975 | Hammond et al. . | |
| 3,949,734 | 4/1976 | Edwards et al. . | |
| 4,135,124 | 1/1979 | Buck | 361/180 |
| 4,137,915 | 2/1979 | Kamen | 128/214 E |
| 4,227,171 | 10/1980 | Masuda et al. | 338/32 R |

*Primary Examiner*—Gene Mancene
*Assistant Examiner*—Michael J. Foycik
*Attorney, Agent, or Firm*—Paul C. Flattery; Daniel D. Ryan; George H. Gerstman

[57] ABSTRACT

Liquid flow sensing apparatus which in the illustrative embodiment is used to sense an occluded vein (cessation of blood flow). A flexible pressure pillow is connected in the blood flow line and is inserted into a housing in contact with a metallic leaf spring. The position of the leaf spring is adjusted relative to an eddy current proximity sensor so that the sensing apparatus is calibrated to a no-alarm position during proper blood flow. If blood flow ceases, the flexible pressure pillow contracts thereby moving the leaf spring away from the eddy current proximity sensor and an alarm condition is thereby detected.

9 Claims, 7 Drawing Figures

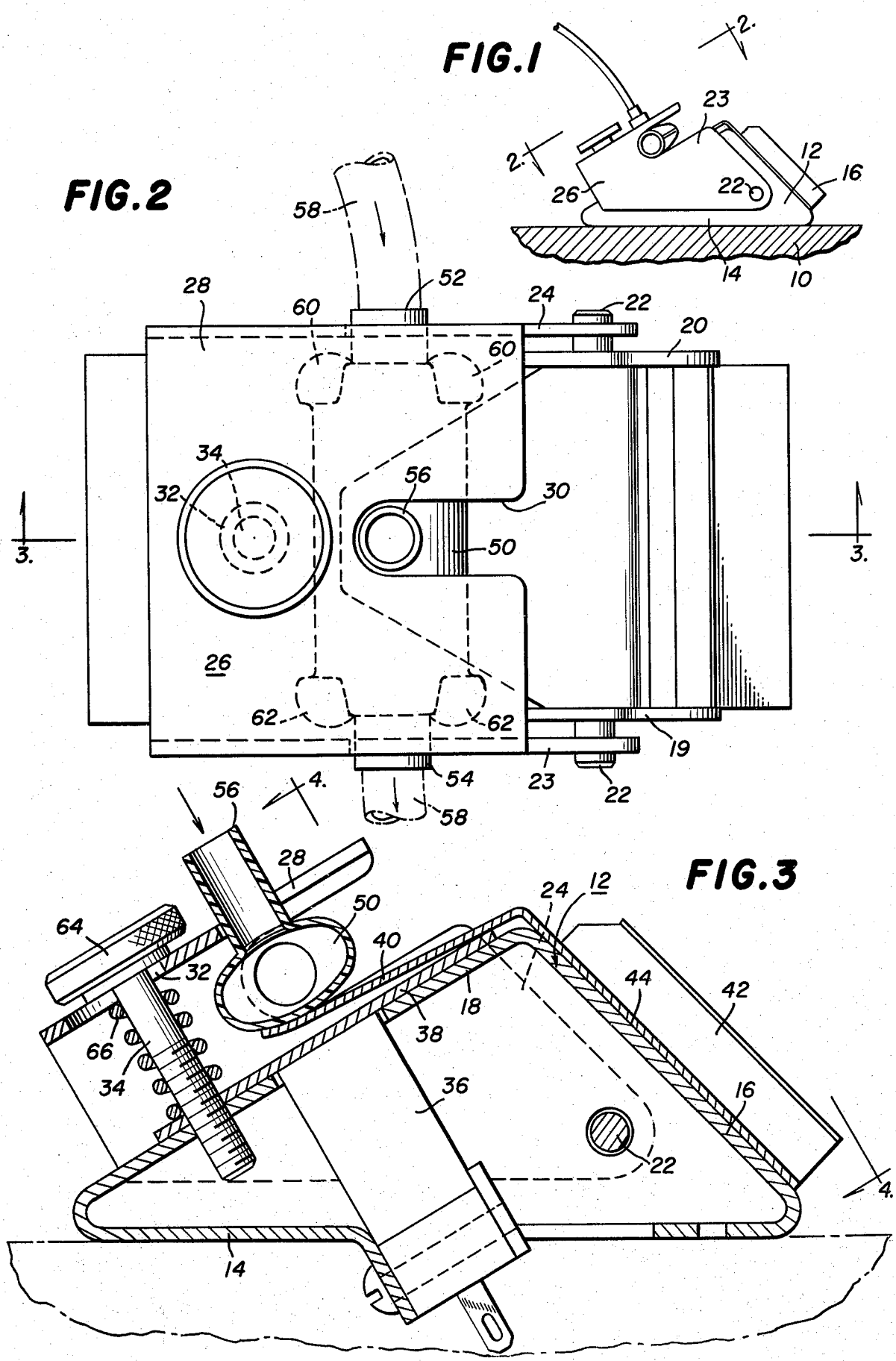

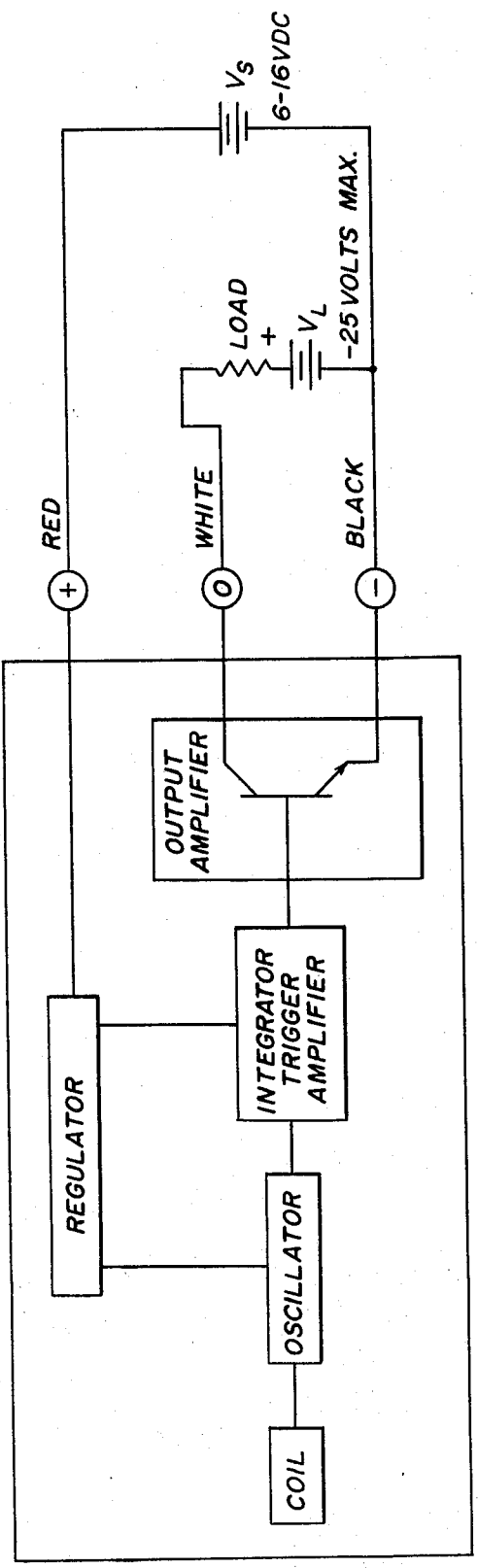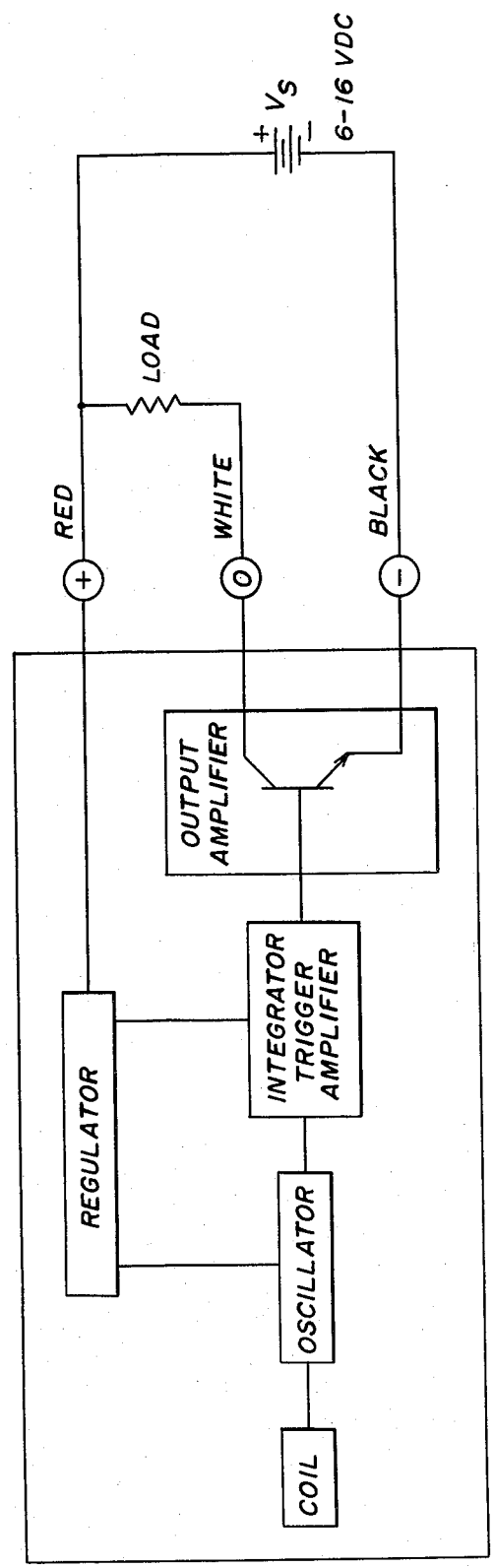

LIQUID FLOW SENSING APPARATUS

BACKGROUND OF THE INVENTION

This invention concerns a novel liquid flow sensing apparatus and, more particularly, a sensing apparatus that is extremely sensitive to cessation of liquid flow and is adapted to be precisely calibrated.

Although the illustrative embodiment of the present invention concerns an occluded vein sensor for use in a membrane plasmapheresis system, it is to be understood that no limitation with respect to usage of the liquid flow sensing apparatus is intended except as set forth in the appended claims.

Plasmapheresis involves the separation of plasma from whole blood, the collection of the plasma and the return of the red cells to the donor. It is desirable, if not essential, that the blood flow be carefully monitored so that an occluded vein is detected. If a vein becomes occluded, it is essential that the withdrawal of blood be terminated immediately.

Precise detecting of the blood flow is therefore necessary, and it is important that the occluded vein sensing device have the ability to be calibrated precisely. It is, therefore, an object of the invention to provide a liquid flow sensing apparatus that is very sensitive to changes in liquid flow.

Another object of the present invention is to provide a liquid flow sensing apparatus that can be calibrated very accurately.

A further object of the present invention is to provide a liquid flow sensing apparatus that can be used as an occluded vein sensor.

A still further object of the present invention is to provide a liquid flow sensing apparatus that is simple in construction and efficient to manufacture.

Other objects and advantages of the present invention will become apparent as the description proceeds.

SUMMARY OF THE INVENTION

In accordance with the present invention, a liquid flow sensing apparatus is provided which comprises a base member and an eddy current proximity sensor carried by the base member. A housing is connected to the base member for receiving a flexible pressure pillow which expands and contracts in response to liquid flow and cessation of liquid flow, respectively.

A metallic spring member is carried by the base member for contact with the flexible pressure pillow. The spring member is movable relative to the eddy current proximity sensor in response to expansion and contraction of the pressure pillow.

The housing includes a platen that is pivotally connected to the base member. Calibration means are provided for initially adjusting the position of the platen to apply a force against the pressure pillow and thereby move the spring member relative to the eddy current proximity sensor.

In the illustrative embodiment, the base member includes a pair of opposed side members and a pivot pin is carried by the side members. The platen includes a pair of side plates that are coupled to the pivot pin.

In the illustrative embodiment, the calibration means includes a spring biased screw coupling the platen to the housing.

In the illustrative embodiment, the liquid flow sensing apparatus is an occluded vein sensor and the flexible pressure pillow comprises a generally pillow-shaped plastic device having a blood flow inlet and a blood flow outlet, and an additional saline inlet is connected to the plastic device and extends generally perpendicular to the blood flow inlet.

In accordance with the present invention, a method is provided for sensing an occluded vein. The method comprises the steps of connecting flexible tubing to a vein and providing a flexible pressure pillow along the tubing. The pillow is inserted into a housing and in contact with a metallic member. The sensing is calibrated by adjusting the housing to move the pillow and the metallic member relative to an eddy current proximity sensor. Thereafter, further movement of the metallic member away from the eddy current proximity sensor is detected.

A more detailed explanation of the invention is provided in the following description and claims, and is illustrated in the accompanying drawings.

BRIEF DESCRIPTION OF THE DRAWINGS

FIG. 1 is a side elevational view of a liquid flow sensing apparatus constructed in accordance with the principles of the present invention;

FIG. 2 is a top plan view thereof, taken along the plane of the line 2—2 of FIG. 1;

FIG. 3 is a cross-sectional elevation taken along the plane of the line 3—3 of FIG. 2;

FIG. 5 is one form of a schematic diagram for wiring the proximity sensor;

FIG. 6 is another form of a schematic diagram for wiring the proximity sensor.

DETAILED DESCRIPTION OF THE ILLUSTRATIVE EMBODIMENT

Figure 4:
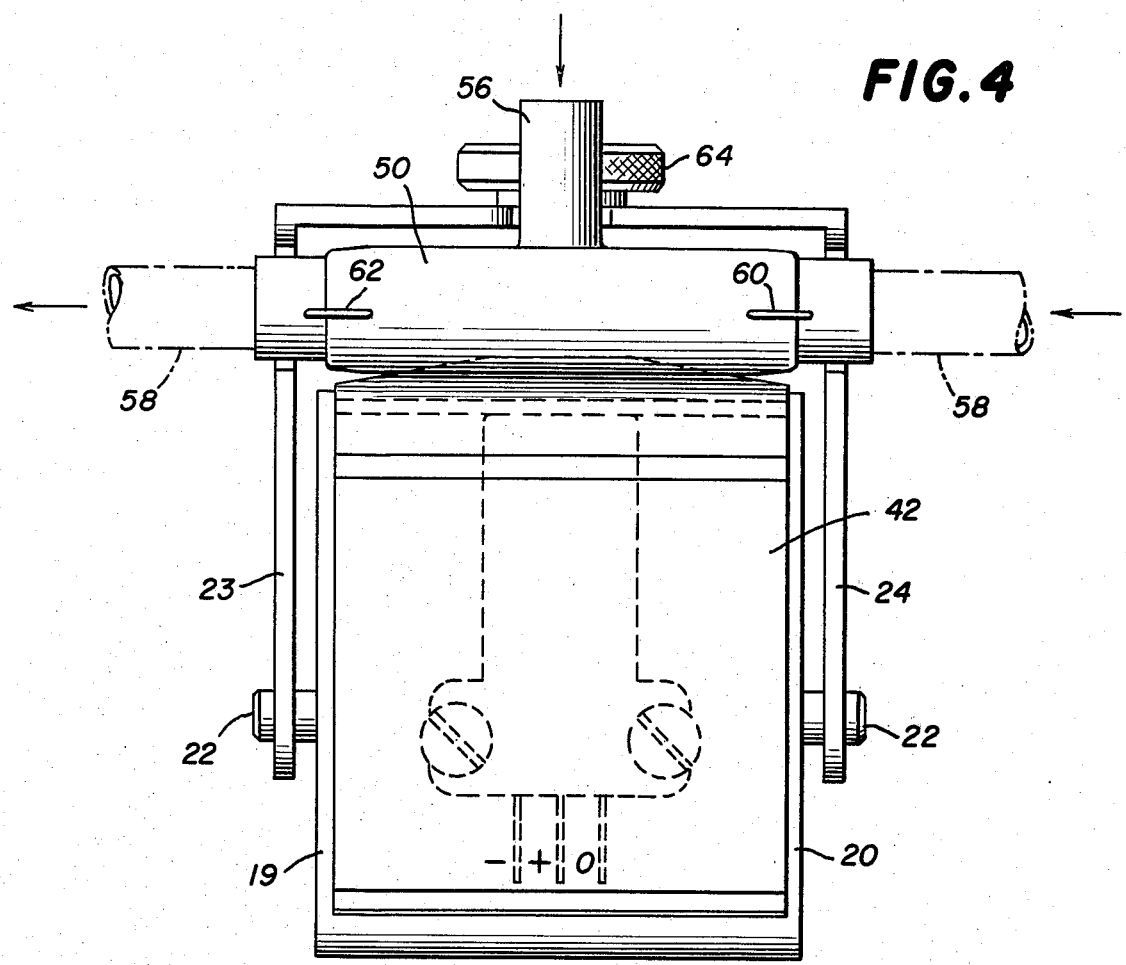
FIG. 4 is a front view of a liquid flow sensing apparatus constructed in accordance with the present invention.

The liquid flow sensing apparatus of the present invention will be referred to as an occluded vein sensor in this detailed description. The occluded vein sensor may be mounted on a plasmapheresis apparatus 10 (FIG. 1). The occluded vein sensor comprises a base member 12 having a generally triangular cross-sectional configuration (FIG. 3) and having a bottom 14, a front portion 16, a top portion 18 and a pair of opposed side members 19, 20. Side members 19, 20 carry a pivot pin 22 to which is connected side plates 23, 24 of a housing 26.

Housing 26 comprises a platen portion 28 which defines a slot 30 and an opening 32 through which an adjustment screw 34 extends. Side plates 23, 24 are integrally formed with platen 28 and extend downwardly from platen 28. It can be seen that housing 26 is pivotable with respect to base member 12, about pivot pin 22.

Although platen 28 is illustrated as being generally planar in the illustrative embodiment, it is to be understood that platen 28 could be curvilinear, if desired.

An eddy current proximity sensor 36, which will be described in more detail below, is carried by base member 12, as illustrated in FIGS. 3 and 4 in particular. A non-metallic spacer 38 is attached to the top surface of top portion 18 of base member 12 and a leaf spring 40 is connected to base member 12 by means of a front panel 42 fastening a fixed portion 44 of leaf spring 40 to the front panel 16 of base member 12. The portion of leaf spring 40 which overlies spacer 38 and eddy current proximity sensor 36 is movable with respect to the eddy current proximity sensor, as seen most clearly in FIG. 3.

Housing 26 is adapted to receive a pressure pillow 50 which is preferably formed of a vinyl plastic material having a generally pillow shape, with a blood inlet 52, a blood outlet 54, and a saline inlet 56 which is connected to the pillow 54 and extends generally perpendicular to the blood inlet 52 and blood outlet 54. Flexible tubing 58 is coupled to inlet 52 and outlet 54 and in series with the patient's vein, while a saline solution is coupled to saline inlet 56 via another flexible tube (not shown). In the illustrative embodiment, pressure pillow 50 is formed by turning a sheet of vinyl plastic material and forming a pair of two-way seals 60, 62. The pressure pillow 50 is insertable into the housing as illustrated, with saline inlet 56 sliding into slot 30.

As illustrated most clearly in FIG. 3, screw 34 includes a thumbwheel 64 for aid in turning the screw and is biased generally upwardly by means of a spring 66. Clockwise rotation of the screw will cause platen 28 to pivot in the counterclockwise direction about pivot 22 (with respect to FIG. 3), thereby essentially bringing the platen closer to top portion 18 of base member 12. The pressure pillow 56 is inserted into the opening defined by the housing in the illustrated manner, with the bottom of pressure pillow 50 resting upon leaf spring 40. Leaf spring 40 is formed of a metallic material. The metallic material may comprise solid steel or the metallic material may comprise an insulative substance coated with or containing metallic foil. As thumbwheel 64 is rotated in the clockwise direction, platen 28 will move the pressure pillow downward to force leaf spring 40 toward proximity sensor 36. In order to calibrate the system, thumbwheel 34 is turned to a no-alarm position. If a vein is occluded or if liquid flow ceases for any reason, the contraction of the pressure pillow 50 will cause the leaf spring 40 to move away from proximity sensor 36, thereby causing an alarm condition.

As a specific example, although no limitation is intended, proximity sensor 36 may be a ferrous metal sensitive XK proximity sensor manufactured by Microswitch of Freeport, Illinois (a division of Honeywell), Model PK8759 0. Microswitch Series XK proximity sensors are ferrous metal sensitive and detect stationary or moving targets. They are actuated without physical contact or attraction between the sensor and the target. Ferrous metal of any thickness or non-ferrous metal foil targets will operate the sensor. The sensor utilizes the eddy current principle. An electromagnetic field is generated by a coil in the face of the sensor. When the field is absorbed by the target, eddy currents are generated in it. These eddy currents present a reflected load to the oscillator, reducing its signal level. This change in level is amplified by the integrator circuitry which drives a Schmitt trigger coupled to an output transistor, switching the load to provide a digital output.

A pair of schematic wiring diagrams for wiring the proximity sensor 36 is illustrated in FIGS. 5 and 6. The "load" may constitute an alarm and/or the liquid pump circuit, whereby movement of the leaf spring away from the proximity sensor causes actuation of the alarm and deactuation of the liquid pump.

Figure 7:
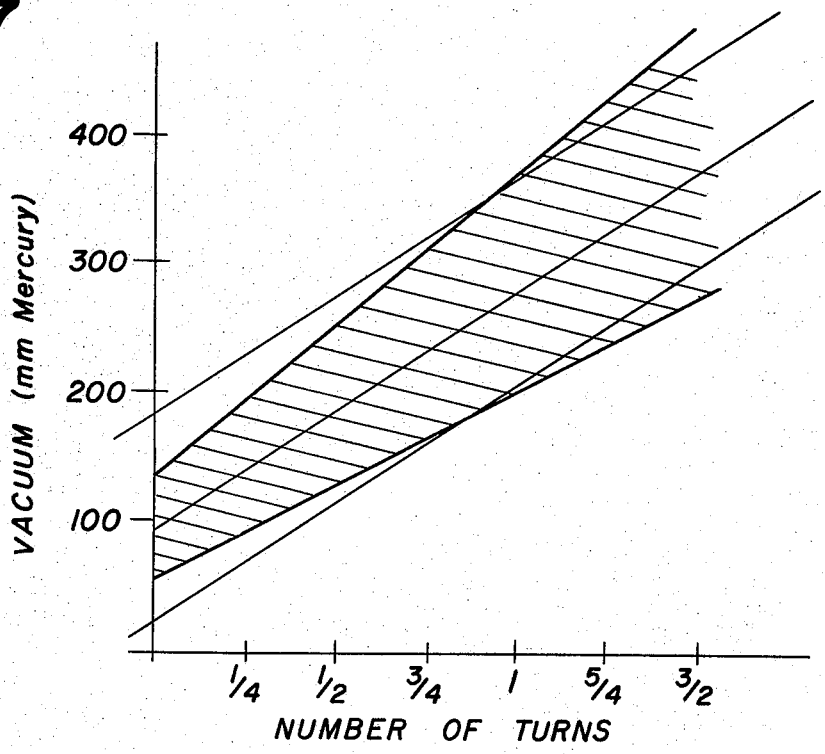
FIG. 7 is a graph used for calibrating the liquid flow sensing apparatus of the present invention.

In FIG. 7, a graph is illustrated for aiding the physician in calibrating the occluded vein sensor. First, thumbscrew 64 is turned clockwise to push the pressure pillow 50 against leaf spring 40, moving the leaf spring 40 closer to the proximity sensor 36, until there is no alarm and/or the liquid pump is operating. Second, if the physician does not want the alarm to be actuated and/or the pump to stop pumping until the line pressure is 200 millimeters of mercury, a horizontal line is extended from the 200 millimeter mark on the vertical axis of FIG. 7 to the shaded portion, which would indicate that the adjustment screw 64 should be turned clockwise further between one-half and three-quarter turns.

It can be seen that a liquid flow sensing apparatus has been provided which enables precise calibration and utilizes an eddy current proximity sensor for providing sensitive detection. Spacer 38 aids in providing the proper spacing for the proximity sensor and also in sealing an occluded vein sensor from blood spills.

Although an illustrative embodiment of the invention has been shown and described, it is to be understood that various modifications and substitutions may be made without departing from the novel spirit and scope of the present invention.

What is claimed is:

1. Liquid flow sensing apparatus which utilizes a flexible pressure pillow which expands and contracts in response to liquid flow and cessation of liquid flow respectively, said apparatus comprising:

a base member;
   an eddy current proximity sensor carried by said base member;
   a flexible metallic spring member carried by said base member for movement toward and away from said eddy current proximity sensor, said spring member being normally biased away from said eddy current proximity sensor;
   a housing pivotally mounted on said base and including means for supporting the pressure pillow with one side of the pillow in contact with said flexible spring member, said support means including platen means contacting the opposite side of the pressure pillow for exerting a measurable force against the opposite pillow side in opposition to the biasing force of said flexible spring member so that, in response to the expansion and contraction of the pressure pillow, only said flexible spring member moves relative to said eddy current proximity sensor; and
   calibration means controlling the pivotal movement of said housing relative to said base for adjusting the magnitude of said measurable force exerted by said platen means against the pressure pillow.

2. Liquid flow sensing apparatus as described in claim 1
   wherein said base member includes a pair of opposed side members and a pivot pin carried by said side members;
   wherein said housing includes a pair of side plates coupled to said pivot pin; and
   wherein said platen means includes a rigid plate extending between said side plates and facing said flexible spring member.

3. Liquid flow sensing apparatus as described in claim 1 or 2 wherein said calibration means includes a spring biased screw coupling said housing to said base member.

4. Liquid flow sensing apparatus as described in claim 3, and further including a non-metallic spacer interposed between said eddy current proximity sensor and said metallic spring member.

5. An occluded vein sensor which comprises:

a base member;

an eddy current proximity sensor carried by said base member;

a flexible pressure pillow which expands and contracts in response to blood flow and cessation of blood flow, respectively, said flexible pressure pillow comprising a generally pillow-shaped plastic device having a blood inlet end and a blood outlet end, and an additional saline inlet connected to said plastic device and extending generally perpendicular to said blood inlet;

a flexible metallic spring member carried by said base member for movement toward and away from said eddy current proximity sensor, said spring member being normally biased away from said eddy current proximity sensor;

a housing pivotally mounted on said base and including means for supporting said pressure pillow with one side of said pillow in contact with said flexible spring member, said support means including platen means contacting the opposite side of said pressure pillow for exerting a measurable force against said opposite pillow side in opposition to the biasing force of said flexible spring member so that, in response to the expansion and contraction of said pressure pillow, only said flexible spring member moves relative to said eddy current proximity sensor;

calibration means controlling the pivotal movement of said housing relative to said base for adjusting the magnitude of said measurable force exerted by said platen means against said pressure pillow.

6. An occluded vein sensor as described in claim 5, wherein said base member includes a pair of opposed side members and a pivot pin carried by said side members;

wherein said housing includes a pair of side plates coupled to said pivot pin; and wherein said platen means includes a rigid plate extending between said side plates and facing said flexible spring member.

7. An occluded vein sensor as described in claim 5 or 6, wherein said calibration means includes a spring biased screw coupling said housing to said base member.

8. An occluded vein sensor as described in claim 7 and further including a non-metallic spacer interposed between said eddy current proximity sensor and said metallic spring member.

9. A method for sensing an occluded vein utilizing an eddy current proximity sensor, which method comprises the steps of:

connecting flexible tubing to a vein;

providing a flexible pressure pillow along said tubing;

positioning said pillow between a rigid platen and a flexible metallic member which is normally biased at a position spaced from the proximity sensor;

calibrating the sensing by moving the rigid platen toward the flexible metallic member to move the pillow and said metallic member against the biasing force of the flexible member toward a position closer to the eddy current proximity sensor than the normally biased position; and thereafter detecting movement of said metallic member toward its normally biased position away from said eddy current proximity sensor in response to contracting of the pressure pillow thereby signifying an occluded vein situation.

* * * * *